United States Patent
Yla-Herttuala et al.

(10) Patent No.: US 6,579,855 B1
(45) Date of Patent: Jun. 17, 2003

(54) ADENOVIRUS-MEDIATED GENE THERAPY

(75) Inventors: Seppo Yla-Herttuala, Kuopio (FI); Anu-Maaria Sandmair, Kuopio (FI); Sami Loimas, Kuopio (FI); Matti Vapalahti, Kuopio (FI)

(73) Assignee: Ark Therapeutics, Ltd. (GB)

( * ) Notice: Subject to any disclaimer, the term of this patent is extended or adjusted under 35 U.S.C. 154(b) by 0 days.

(21) Appl. No.: 09/830,725

(22) PCT Filed: Nov. 5, 1999

(86) PCT No.: PCT/EP99/09017

§ 371 (c)(1),
(2), (4) Date: Jul. 25, 2001

(87) PCT Pub. No.: WO00/28059

PCT Pub. Date: May 18, 2000

(30) Foreign Application Priority Data

Nov. 6, 1998 (GB) .............................. 9824437

(51) Int. Cl.[7] .......................... A01N 43/04; A61K 48/00
(52) U.S. Cl. ....................................... 514/44; 424/93.2
(58) Field of Search ............... 514/44, 93.2; 424/93.21, 424/93.6; 435/320.1

(56) References Cited

U.S. PATENT DOCUMENTS

| | | | | |
|---|---|---|---|---|
| 5,631,236 A | | 5/1997 | Woo et al. ...................... | 514/44 |
| 6,066,624 A | * | 5/2000 | Woo et al. ...................... | 514/44 |
| 6,217,860 B1 | * | 4/2001 | Woo et al. .................. | 424/93.2 |

OTHER PUBLICATIONS

Averett et.al.; 6–Methoxypurine Arabinoside as a Selective and Potent Inhibitor of Varicella–Zoster Virus, 1991, Antimicrobial Agents and Chemotherapy: 851–857.*

Ross et.al.; Assessment of Ganciclovir Toxicity to experimental Intracranial Gliomas following Recombinant Adenoviral–mediated . . . Kinase Gene by Magnetic Resonance Imaging and Proton Magnetic Resonance Spectroscopy, 1995, Clinical Cancer Research, vol. 1: 651–657.*

Eck et.al.; Treatment of Advanced CNS Malignancies with the Recombinant Adenovirus H5.010RSVTK: A Phase I Trial, 1996, Human Gene Therapy 7: 1465–1482.*

Verma et.al.; Gene therapy–promises, problems and prospects, 1997, Nature: 239–242.*

Miller et.al.; Targeted vectors for gene therapy, 1995, FASEB J. 9: 190–199.*

Deonarain; Ligand–targeted receptor–mediated vectors for gene delivery, 1998, Exp. Opin.Ther. Patents 8: 53–69.*

Crystal, Transfer of Genes to Human: Early Lessons and Obstacles to Success, 1995, Science, vol. 270: 404–410.*

Perez–Cruet, M.J. et al. (Nov. 1, 1994) "Adenovirus–Mediated Gene Therapy of Experimental Glomas" *Journal of Neuroscience Research* 39(4):506–511 (US, Wiley–Liss).

Chen Shu–Hsia et al. (1994) "Gene therapy for brain tumors: Regression of experimental gliomas by adenovirus–mediated gene transfer in vivo" *Proceedings of the National Academy of Sciences of the United States of America* 91(8):3054–3057.

Maron, A. et al. (1996) "Gene therapy of rat C6 glioma using adenovirus–mediated transfer of the herpes simplex virus thymidine kinase gene: Long–term follow–up by magnetic resonance imaging" *Gene Therapy* 3(4):315–322.

Driesse, M. J. et al. (Aug. 1998) "Intracerebral injection of adenovirus harboring the HSVtk gene combined with ganciclovir administration: Toxicity study in nonhuman primates" *Gene Therapy* 5(8):1122–1129.

* cited by examiner

*Primary Examiner*—Jeffrey Siew
*Assistant Examiner*—Richard Schnizer
(74) *Attorney, Agent, or Firm*—Saliwanchik, Lloyd & Saliwanchik

(57) ABSTRACT

An adenovirus having a functional thymidine kinase gene is useful in the treatment of brain tumors.

9 Claims, No Drawings

ADENOVIRUS-MEDIATED GENE THERAPY

FIELD OF THE INVENTION

This invention relates to the treatment of brain tumours using gene therapy.

BACKGROUND OF THE INVENTION

The treatment of malignant glioma continues to challenge physicians and scientists. Thymidine kinase gene therapy, using the Herpes Simplex virus thymidine kinase (HSVtk) gene, is one of the most promising treatment modalities, in attempts to change the survival of malignant glioma patients. HSVtk gene therapy is based on the ability of thymidine kinase to catalyze the phosphorylation of ganciclovir (GCV). Phosphorylated GCV acts as a toxic nucleotide analogue, leading to the death of the target cells. This phenomenon is further enhanced by a bystander effect, where neighbouring cells are also destroyed even without transfection. This effect is thought to be due to the release of toxic nucleotide analogues from the transfected cells to neighbouring cells via gap junctions.

Retroviruses and adenoviruses have been used as vectors for gene therapy. Both vectors have certain advantages and limitations. Brain tumours are especially suitable for retrovirus-mediated gene transfer, since retroviruses can only infect proliferating cells while normal, non-dividing brain tissue remains intact. The gene transfer efficiency of retroviruses is relatively low, but could be improved by using retrovirus packaging cells instead of isolated viruses. The transduction time can theoretically be prolonged and the number of transfected cells increased. With retroviruses, the transfected gene incorporates into the genome of the target cell and therefore long-term gene expression can be achieved.

SUMMARY OF THE INVENTION

The present invention is based on the surprising finding that treatment of brain tumours using thymidine kinase gene therapy can be accomplished more effectively if an adenovirus is used as the vehicle to transfer the gene into tumour cells.

According to the present invention, an adenovirus comprises a gene encoding thymidine kinase, and medicaments containing it, are useful for treating a brain tumour. In particular, the tumour is treated following administration of gangciclovir or an equivalent compound.

The thymidine kinase gene will typically be that derived from the Herpes Simplex virus (HSVtk).

The adenovirus/thymidine kinase gene construct is shown to be more beneficial than retrovirus gene transfer.

DESCRIPTION OF THE INVENTION

A construct of the invention can be used to treat a tumour. Treatment may comprise the steps of:
  (i) administering an adenovirus comprising a gene encoding a thymidine kinase, into the wall of the tumour cavity; and
  (ii) administering a compound that forms a cytotoxic compound when phosphorylated.

The compound used in step (ii) may be ganciclovir or a derivative thereof. This method may be used to treat any tumour, preferably a brain tumour, e.g. a malignant glioma. The composition used in step (i) may be administered repeatedly, preferably in 40 to 80 separate applications.

The composition used in the present invention is preferably formulated without the addition of proteins (other than those associated with the adenovirus). This is believed to be preferable to those compositions where albumin is added to reduce the effects of degradative enzymes on the active components. Preferably, this composition comprises glycerol as a stabiliser.

The amount of active products that should be administered to a patient, in use of the invention, can be determined by those skilled in the art, based on information provided herein and on the usual considerations such as the route of administration, the condition being treated and its status, etc.

The following Example illustrates the invention.

EXAMPLE

In this Example, the safety and efficacy of retrovirus packaging cell-mediated and adenovirus-mediated HSVtk gene therapy were compared, for the treatment of malignant glioma. In the trial, retrovirus packaging cell gene therapy did not improve survival of the malignant glioma patients, compared to a lacZ-transfected control group. Tumour progression was present in all patients as evaluated by magnetic resonance imaging (MRI) three months after tumour resection and gene transfer. Adenovirus gene therapy, however, significantly improved the outcome of the patients. Also, in three of the seven adenovirus-treated patients, MRI indicated that the tumours remained stable.

Retroviruses and Retrovirus Packaging Cell Line

A PA317/tk packaging cell line was prepared as described in Poptani et al, Cancer Gene Ther. 5:101–109 (1998). Briefly, 1.2 kb HSV1-TK cDNA (McKnight, Nucleic Acid Res. 8:5949–5964 (1980)) was subcloned into pLXSN retroviral plasmid (Miller et at, Mol. Cell. Biol., 5:2985–3902 (1986)) to create pLTKSN plasmid. Expression of the HSV1-TK is driven by 5' Moloney murine sarcoma virus LTR. The vector also contains an internal SV40 promoter which drives a neomycin resistance (NEO) gene. PA317 cell line was transfected with pLTKSN plasmid using calcium phosphate precipitation. PA317/3.0D5 cell line (PA317/tk) produced 106 cfu/ml retroviruses as determined in 209F fibroblast assay (Ylä-Herttuala et al, J. Clin. Invest. 95: 2692–2698 (1995)). Before injections, packaging cells were expanded, trypsinized and diluted to $10^9$ cells/10 ml Optimem (Gibco BRL). Cells were shown to be free of mycoplasma, other microbiological contaminants and wild-type viruses.

β-galactosidase (lacZ)-containing BAG-retroviruses were produced in φCRIP. Titers of $6\times10^5$ cfu/ml were produced and used as unconcentrated culture supernatant (DMEM, 0.5% NCS, Gibco).

Adenovirus

In HSVtk adenovirus, the expression cassette consisting of human cytomegalovirus (hCMV) enhancer and promoter element -HSV 1-TK cDNA-simian virus 40 (SV40) polyadenylation signal was subcloned into pAdenogal plasmid (Barr et al, Gene Ther. 1:51–58 (1994)) to create pAdCM-VTK plasmid. Linearized pAdCMVTK and sub360 adenoviral DNA (McClane et al, Hum. Gene Ther. 8:739–746 (1997)) were cotransfected into 293 cells (ATCC CRL1573) and recombinant adenovirus, AdCMVTK, was generated through homologous recombination. The virus clone was purified by three rounds of plaque assay and after each round the presence of TK expression cassette in adenovirus genome was confirmed by PCR. Large-scale preparation of AdCMVTK was performed in 293 cells and the virus lysate was purified and concentrated in CsCl gradient, dialyzed and stored at −80° C. Virus titer was determined by plaque assay in 293 cells. Adenovirus preparation was analyzed for integrity of TK expression cassette using restriction enzyme digestion followed by Southern blot analysis. The absence of wild-type replication-competent virus was confirmed by cytopathic assay on HeLa (ATCC CCL-2) and A549 (ATCC CC185) cells. Virus preparation was also tested to be free from microbiological contaminants and lipopolysaccaride (Limulus assay, Sigma).

In lacz, adenovirus nuclear targeted β-galactosidase cDNA under a β-actin promoter and a CMV enhancer was cloned into E1-deleted region of the adenoviral genome using homologous recombination. Adenoviruses were concentrated to titer $3\times10^{10}$ pfu/ml by ultracentrifugation. Purified virus was collected and dialysed with 5 mM Hepes (pH 7.8) and finally in 5 mM Hepes (pH 7.8) containing 20% glycerol.

Patients

Fifteen tumours in 14 patients were treated with HSVtk gene therapy. In addition, 7 control patients were transfected with control lacZ marker gene 4–5 days before resection. All patients had a Karnofsky score over 70. Mean age of the patients was 51 years (range 20–70 years). The tumour was recurrent in 13 cases (59%). All patients received corticosteroids and antiepileptic medication and radiation therapy was used in de novo tumours.

Operation and Gene Transfer

All patients underwent craniotomy and tumour resection. The resection was as radical as possible under the microscope. The diagnosis of malignant glioma was confirmed by frozen sections at the time of the operation. After tumour resection, HSVtk retrovirus packaging cells ($10^9$ cells/10 ml) or adenoviruses ($3\times10^{10}$ pfu/10 ml) were injected into the wall of the tumour cavity in 0.1–0.3 ml quantities, 10 mm deep, with 30–70 injections/patient. GCV treatment (5 mg/kg/d) was delivered intravenously through the subclavian vein twice a day for 14 days. The medication started 14 days or 5 days after the tumour resection and gene transfer in retrovirus or adenovirus patients, respectively. β-galactosidase gene was transferred to seven control group patients via a catheter which was stereotactically inserted into the tumour. The catheter was left in place until the tumour was resected in craniotomy. Gene transfer vectors (BAG retroviruses, titer $6\times10^5$ cfu, and adenoviruses, titer from $3\times10^8$ to $3\times10^{10}$ pfu) were injected into the tumour during three consecutive days, followed by tumour resection 1–2 days later. Patients with β-galactosidase marker gene were not treated with GCV. All patients were treated according to standard clinical practice with radiation therapy.

Magnetic Resonance Imaging

HSVtk-treated patients were followed by MRI on first postoperative day, 4, 8 and 12 weeks after the gene transfer and every second month thereafter. MRI-imaging was done on 1.5 T Magnetom Vision (Siemens) and consisted of T1-weighted (580/14/1=repetition time/echo time/aquicition) axial, coronal and sagittal sequences also after contrast medium (gadopentetatedimeglumine 0,1 mmol/kg); a turbo-T2 weighted (5400/99/2) and FLAIR (fluid attenuated inversion recovery; TR=9000, TE=119, AC=1) sequences. All images were acquired with 5 mm thick contiguous sections and a 256×256 matrix. According to the first postoperative day MRI, surgical resection was graded as total resection, when more than 98% of the tumour volume was removed; subtotal resection, when more than 66% but less than 98% of the tumour volume was removed, and partial resection, when less than 66% of the tumour volume was removed. According to follow-up MRI, tumour behaviour was graded as: progressive when there was even a slightest sign of tumour regrowth, stable when tumour status remained the same, and regressive when tumour volume decreased.

Analysis of Blood, Urine and Tissue Samples

Blood and urine samples were analyzed using routine methods before gene transfer, on the first postoperative day and weekly during hospitalization except for leucocyte differential count which was measured every second day during GCV medication. Anti-virus antibodies were measured before and two weeks after the gene transfer. PCR and wild-type virus assays were performed from plasma and urine samples before gene transfer and 3, 5, 7 and 21 days after the gene transfer.

Histological diagnosis was made from frozen sections at the time of operation and confirmed later with paraffin sections using hematoxylin-eosin and GFAP (Boehringer) stainings. Proliferation activity of the tumours was measured by Ki67 (Dako) staining. After resection, lacZ-transfected tumours were analyzed by X-gal staining as described in Puumalainen el al, Hum. Gene Ther., 9:1769–1774 (1998).

Neuropsychology

Neuropsychological testing was performed in order to determine cognitive functions and quality of life before operation and every second month after the treatment. Evaluation of memory functions used Wechsler Memory Scale (WMS), which contains seven subtests for short-term memory abilities, associated learning test, delayed recall, attention and flexibility of mental processing. Quality of life was measured according to a standardized evaluation of sleeping difficulties, tiredness, memory functions, somatic disorders, mood, sensoric and motoric functions, tenseness, activity, depression, irritation, inefficiency and uncertainity. LacZ-transfected patients were not subjected to neuropsychological testing.

Statistics

Statistical analysis of MRI results was done with Kruskal Wallis test for SPSS. Outcome of the patients was analyzed with Fisher's exact test for SPSS. Statistics for laboratory and neuropsychological analyses was evaluated with Anova for SPSS.

Results

Table 1 shows the results from the gene therapy experiments.

All patients were treated with tumour resection. Retrovirus packaging cells (PA317/tk) were used for seven patients and adenoviruses (Adv/tk) for seven patients. One patient (#) received repeated treatment with PA317/tk cells for two different tumours. Six of the cases were de novo tumours, others were recidives by previous operation (op), radiation therapy (rd) or chemotherapy (ch). Tumour was located in temporal (temp), occipital (occ), frontal (front), or parietal (pariet) lobe. (Sin) indicates the left side and (dx) the right side. Virus antibodies were measured from peripheral blood before and two weeks after the gene therapy. Diagnosis was confirmed as glioblastoma (gb) in 82% of the patients, two patients had anaplastic astrocytoma (aa) and two anaplastic oligodendroglioma (ao). Proliferation activity of the tumours was measured by ki67 immunohistochemical staining. Tumour identity was confirmed by glial fibrillary acid protein (GFAP) immunostaining. Outcome was measured in months and (*) indicates death of the patient. Difference between retro- and adeno-virally treated patients according to survival was significant ($p<0.05$) by Fisher's exact test. The first postoperative MRI was done on 1 or 2 postoperative days after the tumour resection and gene therapy and the second postoperative MRI was done 3 months later. The resection was total if more than 98% of the tumour mass was resected, subtotal if resection was between 66–98% and partial if less than 66% of the tumour was resected. In follow-up MRI the growth was evaluated as progressive adeno-virally treated patients was significant ($p<0.05$).

TABLE 1

| Pat no | Age/Sex | Dg | Tumor location | Ki67 | GF AP | Previous treatment | Gene therapy | Virus ab | 1.postop MRI | 2.postop MRI | Survival months |
|---|---|---|---|---|---|---|---|---|---|---|---|
| 1. | 67/M | gb | occ dx | 20% | + | — | Retro/LacZ | rubella | NA | NA | 3* |
| 2. | 37/M | gb | front sin | 20% | + | op + rad + ch | Retro/LacZ | — | NA | NA | 10* |
| 3. | 63/F | gb | temp dx | 25% | + | — | Adv/LacZ | — | NA | NA | 7* |
| 4. | 44/F | ao | front sin | 25% | + | op + rad | Adv/LacZ | — | NA | NA | 5* |
| 5. | 45/M | gb | temp sin | 40% | + | — | Adv/LacZ | — | NA | NA | 12* |
| 6. | 32/M | ao | front dx | 14% | + | op + rad + ch | Adv/LacZ | adeno 64 | NA | NA | 10* |
| 7. | 39/F | aa | temp dx | 15% | + | op + rad | Adv/LacZ | — | NA | NA | 11* |
| 8. | 36/M | gb | temp sin | 15% | + | — | PA317/tk | — | partial | prog | 13* |
| 9.# | 64/M | gb | occ sin | 14% | + | — | PA317/tk | — | subtotal | prog | — |
| 10. | 44/F | gb | temp dx | 15% | + | op + rad | PA317/tk | — | subtotal | prog | 7* |
| 11.# | 65/M | gb | occ sin | 14% | + | op + rad | PA317/tk | — | subtotal | prog | 8* |
| 12. | 45/F | gb | temp dx | 20% | + | op + rad | PA317/tk | — | subtotal | prog | 9* |
| 13. | 70/F | gb | front sin, multif | 25% | + | — | PA317/tk | adeno 64 | subtotal | prog | 4* |
| 14. | 20/F | gb | temp et pariet dx | 30% | + | op + rad | PA317/tk | — | subtotal | prog | 7* |
| 15. | 56/M | gb | temp et pariet dx | 25% | + | op + rad | PA317/tk | — | subtotal | prog | 4* |
| 16. | 49/F | gb | temp dx | 10% | + | op + rad | Adv/tk | adeno 64 | partial | prog | 12* |
| 17. | 60/M | gb | temp dx | 20% | + | — | Adv/tk | — | subtotal | prog | 10 |
| 18. | 61/M | gb | pariet sin | 30% | + | — | Adv/tk | adeno >256 | partial | prog | 9 |
| 19. | 39/M | aa | front sin | 40% | + | op + rad | Adv/tk | adeno 128 | partial | stable | 8* |
| 20. | 65/M | gb | parieto-occ dx | 20% | + | — | Adv/tk | — | total | stable | 8 |
| 21. | 59/F | gb | frontopariet sin | <1% | + | op + rad | Adv/tk | — | subtotal | stable | 7 |
| 22. | 56/M | gb | pariet sin | 20% | + | op + rad | Adv/tk | — | subtotal | prog¤ | 6§ |

(prog) if there were even slightest sign of the tumour regrowth. Difference in progressive growth between retro- and adenovirally treated patients according to MRI results was significant ($p<0.05$); Kruskal Wallis test. NA=not analyzed.

Gene transfers were clinically safe with both retro- and adenovirus vectors producing no severe adverse effects. However, epileptic seizures were increased in two patients who received adenoviruses although both of these patients had experienced epileptic symptoms previously. One patient had partly reversible hemiparesis and aphasia as a complication of bifocal frontal tumour resection. She had retrovirus packaging cell gene therapy combined with tumour resection. Two patients had fever reactions after adenovirus mediated gene transfer with ventricular openings. The body temperature raised as high as 39.0° C., but the reactions were short term and reversible without any remaining symptoms.

No major alterations were seen in routine laboratory measurements. Only one patient had a mild and reversible leukopenia during GCV treatment without symptoms. Adenovirus antibodies increased remarkably in 3 of 7 Adv/tk-treated patients; two also had a fever reaction. There were no significant changes in liver and kidney functions. No systemic delivery of viruses in plasma and urine samples was detected using PCR and wild-type virus assays. Postmortem samples from one patient were analysed by PCR, which showed that the tumour and all other analyzed tissues were negative for the transgene 6 months after the gene transfer.

MRI follow-up results showed no or very limited effect for retrovirus packaging cell gene therapy. All patients had progressive disease three months after the tumour resection and gene therapy. For adenovirus-mediated gene therapy, MRI results were significantly ($p<0.05$) better with stable disease in 3 out of 7 patients three months after the treatment.

In comparison to the lacZ-treated control group, survival of the patients in the retrovirus group did not show any improvement. The difference between outcome of retro- and adeno-virally treated patients was significant ($p<0.05$).

What is claimed is:

1. A method for inhibiting tumor re-growth in a patient after resection of a brain tumor, wherein said resection creates a cavity defined by a wall of non-tumor tissue; wherein said method comprises the steps of:

(i) administering an adenovirus which comprises a functional thymidine kinase gene operably linked to trancriptional control elements into the wall of non-tumor tissue surrounding the cavity created by the resection of the tumor; and (ii) administering to the patient a thymidine kinase substrate that forms a cytotoxic derivative when phosphorylated through the action of said thymidine kinase;

thereby inhibiting tumor re-growth in the patient.

2. The method, according to claim 1, wherein the compound in step (ii) is ganciclovir.

3. The method, according to claim 1, wherein step (i) or each step comprises injection.

4. The method, according to claim 3, wherein step (i) or each step comprises multiple injections.

5. The method, according to claim 4, wherein step (i) comprises 40 to 80 injections.

6. The method, according to claim 1, wherein said thymidine kinase gene is a Herpes Simplex virus thymidine kinase gene.

7. The method, according to claim 1, wherein said adenovirus is in a medicament which further comprises a stabiliser.

8. The method, according to claim 7, wherein said stabiliser is glycerol.

9. The method, according to claim 1, wherein said brain tumour is malignant glioma.

* * * * *